United States Patent
Giselbrecht et al.

(10) Patent No.: US 9,618,500 B2
(45) Date of Patent: Apr. 11, 2017

(54) VASCULAR MODEL, METHOD FOR PRODUCING SAID MODEL AND USE THEREOF

(71) Applicant: Karlsruher Institut fuer Technologie, Karlsruhe (DE)

(72) Inventors: Stefan Giselbrecht, Karlruhe (DE); Isabella Hebeiss, Widdern (DE); Ute Schepers, Troisdorf (DE); Roman Truckenmueller, Flein (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 126 days.

(21) Appl. No.: 13/924,665

(22) Filed: Jun. 24, 2013

(65) Prior Publication Data
US 2013/0344529 A1    Dec. 26, 2013

(30) Foreign Application Priority Data
Jun. 26, 2012    (DE) .................. 10 2012 105 540

(51) Int. Cl.
*C12M 3/00*    (2006.01)
*C12M 3/06*    (2006.01)
(Continued)

(52) U.S. Cl.
CPC ......... *G01N 33/5005* (2013.01); *C12M 21/08* (2013.01); *C12M 23/16* (2013.01);
(Continued)

(58) Field of Classification Search
None
See application file for complete search history.

(56) References Cited

U.S. PATENT DOCUMENTS 4,713,055 A * 12/1987 Viggiano ................ 435/1.2
4,781,889 A * 11/1988 Fukasawa et al. ........... 422/48
(Continued)

FOREIGN PATENT DOCUMENTS

DE        60112812 T2    6/2006
WO   WO 2009042671 A1   4/2009

OTHER PUBLICATIONS

Chaignaud et al. (Synthetic Biodegradable Polymer Scaffolds, Ed. Atala and Mooney, Birkhauser Boston, p. 1-14, 1997).*
(Continued)

*Primary Examiner* — Allison Fox
(74) *Attorney, Agent, or Firm* — Leydig, Voit & Mayer, Ltd.

(57) ABSTRACT

A vascular model includes at least one microchannel perfusable by at least one fluid and in a form of a hollow structure having a wall thickness in a range from 0.1 μm to 1000 μm, a concave inner surface with a cross-section which is circular in part and at least one pore having a diameter in a range from 1 nm to 100 μm. The at least one microchannel has a width in a range from 0.01 μm to 10 mm and a depth in a range from 0.01 μm to 10 mm. At least one chamber is perfusable by a same and/or different fluid and surrounds the at least one microchannel over an entire length and width or over parts thereof. The at least one chamber adjoins the at least one microchannel. At least one connector is configured to receive and/or discharge the at least one fluid.

19 Claims, 1 Drawing Sheet

(51) Int. Cl.
  *G01N 33/50* (2006.01)
  *C12M 1/00* (2006.01)
  *C12M 1/12* (2006.01)
(52) U.S. Cl.
  CPC ............ *C12M 23/22* (2013.01); *C12M 23/34* (2013.01); *C12M 25/10* (2013.01); *C12M 29/26* (2013.01)

(56) References Cited

U.S. PATENT DOCUMENTS

| 5,015,585 | A | * | 5/1991 | Robinson | ............... | C12M 25/10 |
|---|---|---|---|---|---|---|
| | | | | | | 210/636 |
| 5,320,100 | A | * | 6/1994 | Herweck et al. | ............. | 600/431 |
| 5,395,525 | A | * | 3/1995 | Takano | .................. | B01D 61/28 |
| | | | | | | 210/321.88 |
| 5,698,090 | A | * | 12/1997 | Bene et al. | ....................... | 210/85 |
| 2006/0147487 | A1 | * | 7/2006 | Henderson | .................... | 424/422 |
| 2011/0082563 | A1 | | 4/2011 | Charest et al. | | |
| 2012/0318726 | A1 | | 12/2012 | Charest | | |

OTHER PUBLICATIONS

S. Srigunapalan, C. Lam, A. R. Wheeler, C. A. Simmons, Biomicrofluidics Mar. 2011, 5, 13409.

L. K. Fiddes, N. Raz, S. Srigunapalan, E. Tumarkari, C. A. Simmons, A. R. Wheeler, E. Kumacheva, Biomaterials Feb. 2010, 31, 3459.

J. Shao, L. Wu, J. Wu, Y. Zheng, H. Zhao, Q. Jin, J. Zhao, Lab Chip Aug. 2009, 9, 3118.

J. T. Borenstein, H. Teral, K. R. King, E. J. Weinberg, M. R. Kaazempur-Mofrad, J. P. Vacanti, Biomedical Microdevices Dec. 2002, 4, 167.

M. B. Esch, D. J. Post, M. L. Shuler, T. Stokol, Tissue Eng Part A Dec. 2011.

K. R. King, C. C. J. Wang, M. R. Kaazernpur-Mofrad, J. P. Vacanti, J. T. Borenstein, Advanced Materials Oct. 2004.

R. Lima, S. Wada, S. Tanaka, M. Takeda, K. Tsubota, T. Ishikawa, T. Yamaguchi, World congress on medical physics and biomedical engineering. Berlin Heideberg: Springer Dec. 2006, 283.

R. Lima, S. Wada, S. Tanaka, M. Takeda, T. Ishikawa, K. Tsubota, Y. Imai, T. Yamaguchi, Biomed Microdevices Sep. 2007 153.

M. D. Frame, I. H. Sarelius, Microcirculation Aug. 2000, 7, 419.

A. Abbott, Biology's new dimension Nature Aug. 2003, 424, 870.

J. Deutsch, D. Motlagh, B. Russell, T. A. Desai, Fabrication of Microtextured Membranes for Cardiac Myocyte Attachment and Orientation J Biomed Mater Res Feb. 2000, 53, 267.

N. Sadr, M. Zhu, T. Osaki, T. Kakegawa, Y. Yang, M. Moretti, J. Fukuda, A. Khademhosseini, Sam-Base Cell Transfer Biomaterials Oct. 2011, 32, 7479.

A. D. van der Meer, A. A. Poot, M. H. Duits, J. Feijen, I. Vermes, Microfluidic Technology in Vascular Research J Biomed Biotechnol 2009, Aug. 2009, 823148.

R. A. Knazek, P. M. Guilino, P. O. Kohler, R. L. Dedrick, Science Oct. 1972, 178, 65 Cell Culture On Artificial Capillaries: An Approach to Tissue Growth in vitro.

M. Ikeuchi, K. Ikuta, in Transducers & Eurosensors '07, Lyon, France, Dec. 2007. 1337.

B. Langille, S. Adamson, Relationship between blood flow direction an endotherlial cell orientation Circulation Research Dec. 1981, 48, 481.

R. M. Nerem, M. J. Levesque, J. F. Cornhill, Vascular Endothelial Morphology as an indicator of the Pattern of Blood Flow, J Biomech Eng Aug. 1981, 103, 172.

K. Katoh, Y. Kano, S. Ookawara, Role of Stress Fibers Vasc Health Risk Manag Dec. 2008, 4, 1273.

J. Schanz, J. Pusch, J. Hansmann, H. Wailes, Vascularised human tissue models: a new approach for the refinement of biomedical research, J Biotechn Dec. 2010, 148, 56.

Giselbrecht, S., Gietzelt, T., Gottwald, E., Trautmann, C., Truckenmüller, R., Weibezahn, K.F., and Welle. A., 3D tissue culture substrates produced by microthermoforming of preprocessed polymer films, Biomed Microdevices May 2006, 8, 191-199.

Lindsey K. Fickles, Neta Ray, Suthart Srigunapalan, Ehtan Tumarkan, Craig A. Simmons, Aaron R. Wheeler, Eugenia Kumacheva: "A circular cross-section PDMS microfluids szstem for replication of cardiovascular flow conditions", Biomaterials, Jan. 13, 2010, pp. 3459-3464, vol. 31, Elsevier, Ontario, Canada.

* cited by examiner

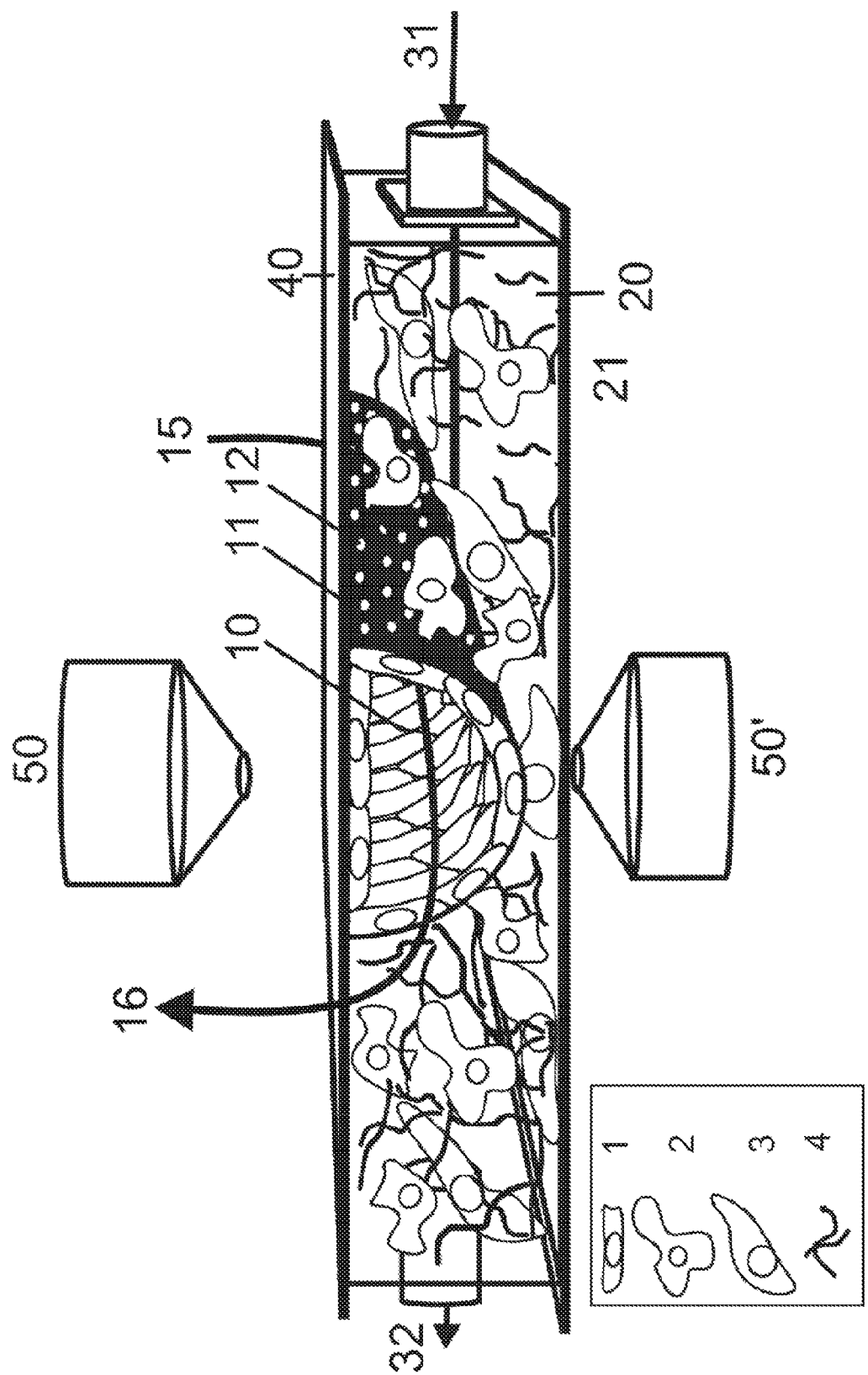

VASCULAR MODEL, METHOD FOR PRODUCING SAID MODEL AND USE THEREOF

CROSS-REFERENCE TO PRIOR APPLICATION

Priority is claimed to German Patent Application No. DE 10 2012 105 540.8, filed on Jun. 26, 2012, the entire disclosure of which is hereby incorporated by reference herein.

FIELD

The invention relates to a vascular model, to a method for producing said model, and to a use thereof for culturing tubular tissue structures, in particular for imitating blood vessels and lymphatic vessels, the blood-brain barrier, lung, gastric or intestinal epithelia and/or glandular structures.

BACKGROUND

Known models for simulating blood vessels and the organotypic culture surrounding them have a large number of drawbacks, in particular with respect to the form of the vessels, the density of different capillaries in the organotypic culture or the porosity of channels which ensure the active supply to the organotypic culture, including gradient formation. However, the complexity of the vascular system requires close to in vivo representation of the physiological conditions, in particular the radii of curvature of the blood vessels, interactions with the extracellular matrix and cells or shear forces.

With known methods for producing microchannel structures, in particular lithography (preferably X-ray, UV or laser radiation), mechanical microstructuring, laser structuring, soft lithography, microreplication methods such as injection moulding or hot stamping, or rapid prototyping methods, microfluidic channels having a rectangular cross-section are usually obtained. Cells which are cultured in channels of this type grow on a planar surface, but this does not correspond to the in vivo conditions [1]. With many microtechnical methods, channels having a round cross-section can be produced in a complex manner, but typically these are not porous [2-6]. However, pores are necessary for supplying cells both from the apical side and from the basolateral side and for examining transendothelial transport processes.

It is known that a three-dimensional tissue which is located in the immediate vicinity of a blood vessel secretes factors which can increase transendothelial transport. This is particularly relevant in the case of tumour tissues, since they secrete and/or recruit proteases which promote short-time breakdown of the endothelial connectivity by proteolysis of what are known as tight junctions, and thus make the blood vessel permeable for active agent transport.

It has been shown that the morphology of the endothelial cells and the correct formation of tight junctions between the endothelial cells in straight rectangular channels differ significantly from those in rounded channels, not only under static conditions but also under fluidic conditions. In addition, flow profiles in rectangular microchannels differ from flow profiles in microchannels having a circular cross-section, whereby the differentiation of the endothelial cells which can be cultured in these channels also varies greatly [2, 7]. Anomalies in the formation and the size of the plasma-rich layer owing to red blood cells were also observed in rectangular fluidic microchannels [8]. Morphology studies on endothelial cells in microchannels having rectangular and circular cross-sections showed that there are particularly great differences in the correct formation of the actin cytoskeleton and the focal adhesion points [9]. The morphology of the endothelial cells and the correct formation of tight junctions between the endothelial cells differ significantly not only under fluidic conditions but also under static conditions.

A three-dimensional structure corresponding to the natural environment represents the in vivo situation of the cells better than a planar surface [10-12]. Since the vascular system is a complex cellular system, it is very important for an in vitro system to provide as far as possible the physiological environment, in particular curvature of the vessel structures, composition of the extracellular matrix, fluidics, shear force ratio, density of supply to the three-dimensional tissue with channels at small intervals, branching of the channels [12, 13]. Most microfluidic channel structure systems are produced from polydimethylsiloxanes (PDMS) by soft lithography. In [2], a microfluidic channel system made of PDMS and having a circular cross-section is presented, which system makes it possible to imitate and examine cardiovascular flow conditions in endothelial cells. However, this system is not suitable for examining transendothelial transport of active agents in tissue, since these are closed channels, the outer shell of which consists mainly of a collagen matrix.

At present, there are various artificial models of round perfused channels based on hollow fibres as artificial blood vessels [14]. However, in all hollow fibre systems, gradients can occur in the longitudinal and the radial direction of the fibres, since the culture medium must take a particular route from the capillary inlet to the capillary outlet, along which route the cells deplete the nutrients in the culture medium. The provision of nutrition and blood flow through blood vessels is a significant unsolved problem in the establishment of an organotypic model. Even in the case of small tissue volumes it is important to implement a vascular system or a corresponding equivalent, since for distances of more than approximately 100-300 μm to the nearest blood capillary the diffusion is no longer sufficient for nutrition. There is therefore a need recognized in the present invention for models in which supplying blood vessels can be cultured in combination with any desired tissue and which also meet the requirements of a (micro)vascular system. The provision of a physiologically correct, three-dimensional arrangement is thus required, and this has not yet been achieved with conventional hollow fibre systems, since hollow fibres allow neither branching nor frequent change of the cross-sections.

Systems as described in [19] are based on the repopulation of acellularised porcine small intestine segments, the vascular system of which is repopulated with endothelial cells. Various three-dimensional tissues can be cultured on the outer surface of the blood vessels and can be supplied via the repopulated blood vessels. However, the system needs further optimisation with regard to the supply to the tissue. The variability in the explantation and acellularisation leads to different qualities of the individual matrices. Moreover, this model cannot be used as a single-use product for testing in the high-throughput method.

In [15], a very simple strategy for the use of thermoformed, thin-walled and porous channels for supplying thick three-dimensional tissues is proposed. However, this document does not consider active perfusion of the channels for supplying the cells. Cells in the hydrogel are supplied only by diffusion from the channels, which are not actively perfused.

SUMMARY

In an embodiment, the present invention provides a vascular model. At least one microchannel is perfusable by at least one fluid and is in a form of a hollow structure having a wall thickness in a range from 0.1 µm to 1000 µm, a concave inner surface with a cross-section which is circular in part and at least one pore having a diameter in a range from 1 nm to 100 µm. The at least one microchannel has a width in a range from 0.01 µm to 10 mm and a depth in a range from 0.01 µm to 10 mm. At least one chamber is perfusable by at least one of a same and a different fluid and surrounds the at least one microchannel over an entire length and width of the at least one microchannel or over parts thereof. The at least one chamber adjoins the at least one microchannel. At least one connector is configured to at least one of receive or discharge the at least one fluid.

BRIEF DESCRIPTION OF THE DRAWING

The present invention will be described in even greater detail below based on the exemplary FIGURE. The invention is not limited to the exemplary embodiment. All features described and/or illustrated herein can be used alone or combined in different combinations in embodiments of the invention. The features and advantages of various embodiments of the present invention will become apparent by reading the following detailed description with reference to the attached FIGURE which shows a schematic, not-to-scale representation of a vascular model according to an embodiment of the invention.

The FIGURE shows a schematic representation of a vascular model according to an embodiment of the invention.

DETAILED DESCRIPTION

In an embodiment, the present invention provides a vascular model, a method for producing said model and a use thereof which overcome the aforementioned limitations and drawbacks of the prior art that are recognized in the present invention.

According to an embodiment of the invention, a vascular model is provided which has at least one thin-walled, that is to say having a wall thickness of from 0.1 µm to 1000 µm, preferably of from 1 µm to 100 µm, and porous microchannel having curved inner faces and at least one chamber which surrounds the microchannel and which can also be perfused actively by a fluid, that is to say a liquid or a gas, in which particles can be introduced, for in vitro imitation of tubular, in particular three-dimensional tissue structures and the directly adjacent tissue, that is to say in particular blood vessels and lymphatic vessels, blood-brain barrier, lung, gastric or intestinal epithelia or glandular structures, for example pancreas.

The at least one microchannel has a curved, preferably semi-circular cross-section, and this reflects the natural shape and the natural radii of curvature of an in vivo blood vessel. The dimensions of the at least one microchannel are adapted in accordance with the blood vessels to be modelled. The five most important blood vessels are:

arteries, diameter larger than 1 cm in elastic arteries and 0.1-10 mm in muscular arteries;
arterioles, diameter 10-100 µm;
capillaries, with diameter 4-10 µm;
venules, diameter 10-100 µm; and
veins, diameter 0.1 mm to more than 1 mm.

The vascular model has at least one curved or rounded hollow structure which is preferably made in a thin film having a wall thickness of from 0.1 µm to 1000 µm, preferably of from 1 µm to 100 µm, and is in the form of at least one microchannel, and at least one pore, more preferably a plurality of pores, which are preferably statistically distributed and/or regularly arranged, in the wall of the channel. The at least one pore is preferably round, square, star-shaped or cylindrical, single conical, double conical [hourglass shape] or cigar-shaped and is preferably made in the film by means of ion track technology. The pore size is in the range of from 1 nm to 100 µm, preferably of from 10 nm to 10 µm, while the pore density is in the range of $1$-$10^9$ pores/cm$^2$, preferably of $10^5$-$10^6$ pores/cm$^2$.

The film for the channel structure of the vascular model preferably consists of a thermoplastic polymer, more preferably of polymethyl methacrylate (PMMA), polycarbonate (PC), polyethylene terephthalate (PET), polystyrene (PS), polyimide (PI), polypropylene (PP), polyvinylidene fluoride (PVDF) or cycloolefin copolymer (COC or COP). The film can already be porous prior to forming; in particular it can be in the form of an ion track membrane, non-woven, or phase separation membrane.

In a preferred configuration, the channel structure is preferably connected by thermal bonding to a cover (plate), the thickness of which is in the range of the film, in order to close the at least one microchannel in a permanent (rigid) or releasable manner.

The at least one microchannel and/or the at least one chamber and/or the cover is/are preferably highly transparent and has/have a low autofluorescence, preferably at the typical excitation wavelengths which are used for imaging and optical analysis systems, in particular for UV/VIS, IR or Raman.

In a particularly preferred configuration, the cover has at least one opening, preferably a plurality of openings, in the region of the channel lumen. The material for the cover can be selected from a variety of materials, preferably from plastics material, glass, metal or ceramic material.

The configuration of the at least one microchannel (channel) can vary over the length of the channel. The following different arrangements are preferred in this connection:

straight; and/or
branched, in particular in the form of a vascular tree; and/or
parallel channels side by side.

At least the following are provided:

one straight channel or a plurality of parallel straight channels and/or
curved channels with radii of curvature, minimum radii of curvature corresponding to 0.2 times the local wall thickness, such that concave inner faces of the channel have radii of curvature in a range of from 0.02 µm to 10000 µm, preferably of from 5 µm to 5000 µm, more preferably of from 10 µm to 1000 µm, and/or
branched channels, that is to say division of a branch into at least two branches.

The width of the channels is in a range of from 0.01 µm to 10000 µm, preferably of from 5 µm to 5000 µm, more preferably of from 10 µm to 1000 µm.

The depth of the channels is in a range of from 0.01 µm to 10000 µm, preferably of from 5 µm to 5000 µm, more preferably of from 10 µm to 1000 µm.

At least one connector makes it possible to connect a pump system to the channel. The at least one connector is attached to at least one chamber and/or, in a particularly advantageous configuration, additionally mounted on the cover and connected thereto, in particular by thermal bonding, adhesive, adhesive tape, ultrasonic welding or laser beam welding, or was already made or produced during production, preferably by injection moulding.

The vascular model comprises at least one chamber (compartment) which is directly adjacent to the channel. The at least one chamber surrounds the channel over its entire length and width or only parts thereof; the height of the at least one chamber is limited to 1 mm, a particularly preferred height being from 200 µm to 500 µm, the geometry of the at least one chamber being adapted in accordance with the application.

A preferred configuration of the chamber is a circular compartment which surrounds the channel at least in part; particularly preferred is a chamber which completely surrounds the channel and has a similar geometry to the channel, but both the depth and the height are greater by 500 µm, more preferably 300 µm.

In a particular configuration, at least a second chamber according to the specifications of the first chamber surrounds said first chamber at least in part, producing a double- or multi-nested structure.

In an alternative configuration, a chamber is subdivided into a plurality of smaller compartments which each surround only subregions of the channel structure.

A vascular model according to an embodiment of the invention further comprises at least one connector for receiving and or discharging the at least one fluid.

In a particularly preferred configuration, both the cover which closes the at least one channel in a preferred configuration and the at least one microchannel have at least one connector, which in particular may be in the form of an opening and which allows access from the outside and/or connection of the compartment to a further circulation system having at least one pump. With at least two connectors, continuous perfusion of the at least one chamber is possible. If more than one connector is provided, the connectors are provided with further accesses, preferably via openings, in a similar manner and are preferably positioned in alignment one above the other in an axially centred manner.

A method according to an embodiment of the invention for producing a vascular model according to an embodiment of the invention comprises at least the following steps:
producing at least one microchannel having a cross-section which is circular in part by forming a film into a hollow structure which has a wall thickness of from 0.1 µm to 1000 µm, the film already having one or a plurality of pores prior to forming and/or one or a plurality of pores being made in the film or produced in the film after forming, and
attaching at least one chamber to the at least one microchannel in such a way that said chamber surrounds the at least one microchannel over its entire length and width or over parts thereof.

In a preferred method, micro-thermoforming is used to form the channel structure. In this context, the film is formed in the entropy-elastic state and not in a melt phase, meaning that, if required, pre-treatments, in particular heavy ion radiation, can be preserved. Heavy ion radiation ensures penetration of the film. The angle of radiation is preferably selected to be perpendicular to the surface and masks are used for local limitation of the region to be irradiated or for locally limited opening of the pores in the etching step.

In this way, a channel structure having a cross-section which is circular, preferably semi-circular, in part can be produced. In the case of heavy ion radiation, chemical etching then takes place in order to dissolve the physically modified regions within the film, which are known as latent ion tracks. In this context, the pore size is adapted to the selected experiment, for example for the passage of molecules or cells, by varying the etching parameters.

In an alternative configuration, already porous films of layered structures, in particular non-wovens or phase separation membranes, are used and are formed into the desired channel structures.

In a particularly preferred method, thermal bonding of a second, porous or preferably non-porous polymer film for covering the channel takes place, which film is provided in a preferred configuration with the corresponding holes for the fluidic contacting. Alternatively, other connection methods, in particular ultrasonic welding, laser welding or adhesion, are used in this context.

Finally, the at least one microchannel is preferably joined to at least one external pump system for supplying the cells with medium, in order to examine reactions of the cells to applied shear forces. In this way, the in vivo situation can be imitated in the vascular model.

A chamber is preferably produced from a plurality of modules, in particular from an annular spacer made of biocompatible material, preferably plastics material, glass, silicon or ceramic material, and a preferably circular, thin, transparent glass disc or plastics material film, which in particular has a low autofluorescence at the typical excitation wavelengths for imaging and optical analysis systems (UV/Vis, IR, Raman, etc.). The spacer is connected to the film in which the at least one channel is made, and to the material from which the chamber is made, by conventional methods, in particular adhesion, thermal bonding, ultrasonic welding or laser welding.

A particularly preferred production method is thermoforming; in this connection transparent, thin, single- or multi-layer films can be brought into the corresponding shape. By selecting suitable polymers and layers, including inorganic or metal layers, gas permeability, in particular to oxygen, water vapour permeability and further properties such as optical transparency or elasticity are controlled.

In a particularly preferred configuration, both the glass disc and plastics material films of the at least one chamber are also provided with further openings for connectors and with pores which are arranged in a statistically distributed or regular and/or defined manner, in order to allow exchange of gases, liquids, particles, cells, etc. with the environment or with the further chambers enclosing the chamber in question on the side of the vascular model remote from the channel film, too.

The device according to an embodiment of the invention has in particular the following advantages. Serial, repeated population, optionally with different cell types, is made possible, as is an active supply to the three-dimensionally cultured cells in the surrounding chamber by active perfusion of this chamber.

Substances are exchanged between the surrounding chamber and the lumen of the microchannels through the porous walls of the channels in both directions for examination of substance transport, transport of signalling and messenger substances, active agents, viruses and bacteria, particulate and filamentary foreign bodies, migration of cells, etc. In this context, either direct interaction and physical contact between the cells in the lumen and the cells in the chamber or only the exchange of soluble factors is possible, depending on the pore size. A physical and/or chemical gradient between the channel lumen and the surrounding compartment can be produced via the porous, thin wall of the channel and a cell layer which may be located thereon.

Active perfusion of the environment of the at least one porous microchannel is made possible by producing a perfusable chamber. The surrounding chamber can also be used for culturing artificial three-dimensional tissues, in particular by means of inserted hydrogels, (electrospun) fibres, non-wovens, textile structures, or porous, spongy structures for imitating a biological unit consisting of tubular or vessel-like structure and surrounding tissue.

A lower compartment allows endothelial cells in the porous microchannel to be supplied from the basolateral side, too. This makes it possible to co-culture different cell types, to represent different tissue types associated with the blood vessel system, for example connective tissue cells. It is possible to culture tumour cells in the lower compartment in order to represent tumour tissue in the form of a cancer model. The lower compartment can be operated statically and actively, for example by removing a type of lymph. A direct connection to an analysis system (mass spectrometry, Raman, IR) for detecting transendothelial transport or metabolic processes within the vascular system is also possible.

The model according to an embodiment of the invention allows quasi in vivo representation of a blood vessel system in vitro. Varying the size and shape of the channel structures makes it possible to represent different vessel types (arteries, veins, arterioles, capillaries). Microfluidic use makes it possible to imitate the blood flow within the blood vessel/the tissue. It is thus possible to examine the endothelium under fluidic conditions and transendothelial processes.

Owing to the use of transparent materials, to a thin-walled construction and to the outer dimensions, short-term or longer-term operation and microexamination of the model on a standard microscope stage comprising an incubation system are possible. The transparency of the components allows direct visualisation of transendothelial transport processes by means of microscopy.

Particularly advantageous is the simple and reproducible construction of the vascular model according to an embodiment of the invention, which construction makes it possible to produce large quantities cost-effectively and thus makes the model accessible as a cost-effective single-use system in particular for screening. Irrespective of this, owing to active and dynamic perfusion of the channels and/or chambers, the model can be combined with corresponding analytics, in particular with upstream and/or downstream flow-through cells for infrared, Raman, etc.

Preferred uses are in the examination of active agents, half-lives or blood circulation times and endothelial uptake or transendothelial transport of different substances.

The present vascular model can be used to imitate tubular structures of the body, in particular glandular structures, intestinal epithelia, lung epithelia or kidney channels, but a model of the blood-brain barrier is also conceivable. The model makes it possible to examine inflammation reactions, for example the chemokine-/zytokine-dependent transendothelial migration of blood cells (leukocytes, monocytes, etc.).

The FIGURE shows a schematic, not-to-scale representation of a vascular model according to an embodiment of the invention, comprising an artificial blood vessel in the form of a microchannel 10, which is surrounded by an adjacent chamber (compartment) 20, mutually independent circulations flowing through the microchannel 10 and the chamber 20.

The microchannel 10 has a wall in the form of a hollow structure 11, in which a plurality of pores 12 is made. A fluid flows through the microchannel 10 in the direction 15→16, a first circulation forming as a result.

The chamber 20 which surrounds the microchannel 10 comprises a transparent base plate 21 and two connectors 31, 32, a second circulation which moves a fluid in the direction 31→32 forming as a result.

A microfluidic perfusion system is connected to the microchannel 10 and the chamber 20 so as to allow the supply to the cells 1-4 contained in the channel and/or for carrying away lymph or the transendothelially transported analytes for detecting the transendothelial transport.

The microchannel 10 is provided with a transparent cover 40 which closes the microchannel 10 in a releasable manner and limits the chamber 20 in part.

The present construction of the vascular model and the selection of transparent materials for the individual components makes it possible to observe processes within the vascular model by means of the lenses 50, 50'.

The FIGURE shows by way of example a use according to an embodiment of the invention of the vascular model. In this context, endothelial cells 1, organ-specific cells 2, fibroblasts 3 and/or a biologically decomposable matrix 4 grow at different points in the vascular model and form an artificial, supplying blood vessel system which takes on the distribution of the perfusion medium and thus the supply to the organotypic 3D cell culture surrounding the microchannel 10 in the chamber 20.

The population took place by injection with suspended cells, optionally repeatedly, optionally sequentially, with firstly endothelial cells for the vessels, and then mesenchymal cells or similar organotypic cell cultures being introduced into the chamber 20. This type of population can be applied to virtually any desired vascularised organotypic cell cultures.

The vascular model according to an embodiment of the invention comprises a polycarbonate film (PC film) which has been thermoformed by means of what is known as SMART technology [20] and which has a thickness of 65 μm. The thermoforming took place at a mould temperature of 157° C. and a gas pressure of 2.6 MPa; the ejection temperature was 70° C.

After thermoforming the membrane had a thickness of 25 μm at the thinnest point. The microchannel 10 had the following dimensions:
length 20 mm,
width 1 mm,
depth 250 μm.

Straight or branched channels were produced; width and depth were varied.

The thermoformed film was chemically etched with sodium hydroxide solution in order to open the pores. The etching took place over 4.5 h. Pore sizes of 4-8 μm at a pore density of $10^6$ pores/cm$^2$ were obtained.

The bonding of the porous thermoformed PC film to a non-porous PC film, in order to close the channel by means of a cover 40, took place at a temperature of 147° C. The bonded thermoformed film was glued to a block of PMMA comprising previously milled Luer connectors which allow the connection of a hose system. The microchannel 10 and/or the chamber 20 could be filled via the Luer connectors. A chamber 20 having a height of 500 μm and a diameter of 24 mm was attached by gluing on a silicon ring and closing with a small cover glass.

For coating of the inner face of the channel with fibronectin, a fibronectin solution with a concentration of 1 mg/ml in distilled water was introduced into the channel and incubated for 4 h at room temperature. The channel was washed with PBS (phosphate buffered saline). The channel and the lower chamber were filled with medium and conditioned overnight in the incubator at 37° C. and 5% $CO_2$.

A cell suspension of human umbilical vein endothelial cells (HUVECs) 1 with $5 \times 10^6$ cells/ml was introduced into the channel directly via the connectors and incubated for 10 min in the incubator. Then a cell suspension was again introduced into the channel and the entire vascular model was rotated through 90° and incubated for 10 min again. This was done two more times in order to ensure complete population of the microchannel 10 with endothelial cells 1. After introduction of the endothelial cells 1 into the microchannel 10 these were cultured for a further 3 h in order to allow the rigid adhesion thereof to the hollow structure 11. The channel was then connected to a pump system comprising a medium reservoir in order to ensure the supply of fresh medium to the cells. The chamber 20 was either operated statically or connected to a pump system by means of the connectors 31, 32. The endothelial cells 1 were cultured in the microchannel 10 under fluidic conditions (500 μl/min). As a result, shear forces produced corresponded to the shear forces present in blood vessels in vivo.

This resulted, after culturing for three or more days under fluidic conditions, firstly in orientation of the endothelial cells 1 in the direction of the media flow 15→16 in the microchannel 10. This result corresponds to the in vivo situation [16, 17]. There was also formation of stress fibres in the flow direction 15→16 in response to the occurring shear forces. "Stress fibres" is understood to mean thick bundles of actin filaments, cross-linked proteins and myosin II [18].

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

What is claimed is:

1. A vascular model comprising:
   at least one man-made chamber including a cover and a base plate,
      wherein the cover and base plate are formed of a plastic material film or of glass discs,
      wherein the at least one man-made chamber is perfusable by at least one of a first fluid and a second fluid;
   at least one microchannel in the form of a hollow channel structure,
      wherein the at least one microchannel is formed of a thin film wall made of a thermoplastic polymer,
      wherein the thin film wall of the microchannel has a thickness in a range from 0.1 μm to 1000 μm and has at least one pore having a diameter in a range from 1 nm to 100 μm,
   the at least one microchannel being at least partially surrounded by the at least one man-made chamber,
      wherein the at least one microchannel is perfusable by at least the first fluid,
      wherein at least a portion of the at least one microchannel is bonded directly to the cover of the man-made chamber along the length of the microchannel, such that the portion of the microchannel bonded to the cover has a semi-circular cross-section,
   the portion of the at least one microchannel having a semi-circular cross-section having a width in a range from 0.01 μm to 10 mm and a depth in a range from 0.01 μm to 10 mm;
   at least one first connector in fluidic communication with a lumen of the at least one microchannel and configured to at least one of receive or discharge the at least one first fluid; and
   a first pump system connected to the lumen of the at least one microchannel via the at least one first connector.

2. The vascular model according to claim 1, wherein the at least one microchannel is straight.

3. The vascular model according to claim 1, wherein the at least one microchannel includes at least one division into at least two branches.

4. The vascular model according to claim 1, wherein the at least one microchannel has a radius of curvature in a rage from 0.01 μm to 10000 μm.

5. The vascular model according to claim 1, wherein the at least one man-made chamber comprises at least two man-made chambers, and wherein at least a second man-made chamber surrounds a first man-made chamber which at least partially surrounds the at least one microchannel in such a way that a nested structure is formed.

6. The vascular model according to claim 1, wherein the at least one man-made chamber comprises at least two man-made chambers, and wherein each of the at least two man-made chambers surrounds different subregions of the at least one microchannel.

7. The vascular model according to claim 1, further comprising a layer of three-dimensionally cultured cells located on an exterior surface of the portion of microchannel having the semi-circular cross-section.

8. The vascular model according to claim 7, further comprising a medium reservoir,
   wherein the first pump system is configured to supply, via the lumen of the at least one microchannel, medium from the medium reservoir to the three-dimensionally cultured cells on the exterior of the microchannel, and
   wherein the cells are selected from the group consisting of endothelial cells, organ-specific cells, fibroblasts, and suspended cells.

9. The vascular model according to claim 1, further comprising an endothelial cell culture disposed on the inner surface of the at least one microchannel.

10. The vascular model according to claim 1, wherein one or more of the at least one microchannel, the cover, and the base plate are transparent.

11. The vascular model according to claim 1, wherein the cover is bonded to at least a portion of the at least one microchannel by thermal bonding.

12. The vascular model according to claim 1, wherein the cover is bonded directly to the hollow channel structure along a length of the hollow channel structure that extends in a direction of fluid flow through the microchannel.

13. The vascular model according to claim 1, further comprising:
at least one second connector in fluidic communication with the at least one man-made chamber and configured to populate the man-made chamber with cell cultures and at least one of receive or discharge the first fluid or the second fluid; and
a second pump system connected to the at least one man-made chamber via the at least one second connector.

14. The vascular model according to claim 13, wherein the first pump system connected to the lumen microchannel is configured to perfuse the first fluid into the lumen of the at least one microchannel to form a first circulation,
wherein the second pump system connected to the at least one man-made chamber via the at least one second connector is configured to perfuse the second fluid into the at least one man-made chamber to form a second circulation, and
wherein the first circulation and the second circulation are mutually independent.

15. The vascular model according to claim 1, wherein the semi-circular cross-section of the at least one microchannel is linear in a region where the cover is bonded to the hollow channel structure and is curved elsewhere.

16. The vascular model according to claim 1, wherein the thin film wall has a thickness in a range of from 0.1 µm to 100 µm.

17. A method for producing a vascular model, comprising:
providing at least one man-made chamber including a cover and a base plate,
wherein the cover and base plate are formed of a plastic material film or of glass discs,
wherein the at least one man-made chamber is perfusable by at least one of a first fluid and a second fluid;
producing at least one microchannel in the form of a hollow channel structure from a thin film wall material made of thermoplastic polymer,
wherein the thin film wall material has a thickness in a range from 0.1 µm to 1000 µm, and
wherein at least one of:
the thin film wall material already comprises at least one pore having a diameter in a range of from 1 nm to 100 µm prior to forming the microchannel, or
at least one pore having a diameter in a range from 1 nm to 100 µm is made in the thin film wall material or produced in the thin film wall material after forming the microchannel;
placing at least a portion of the at least one microchannel into the at least one man-made channel;
bonding at least a portion of the at least one microchannel directly to the cover of the at least one man-made chamber along a length of the at least one microchannel, such that the portion of the microchannel bonded to the cover has a semi-circular cross-section,
wherein the portion of the at least one microchannel having a semi-circular cross-section has a width in a range from 0.01 µm to 10 mm and a depth in a range from 0.01 µm to 10 mm;
providing a first pump system; and
coupling the first pump system to a lumen of the at least one microchannel.

18. A method of using a vascular model, comprising:
providing the vascular model of claim 1; and
culturing tubular tissue structures on at least one surface of the at least one microchannel or inside the at least one chamber.

19. The method according to claim 18, wherein at least one of blood vessels and lymphatic vessels, the blood-brain barrier, lung, gastric or intestinal epithelia, or glandular structure are imitated.

* * * * *